United States Patent
Hiraoka et al.

(10) Patent No.: US 11,254,634 B2
(45) Date of Patent: Feb. 22, 2022

(54) METHOD FOR PRODUCING AT LEAST ONE OF UNSATURATED ALDEHYDE AND UNSATURATED CARBOXYLIC ACID AND CATALYST FOR PRODUCING AT LEAST ONE OF UNSATURATED ALDEHYDE AND UNSATURATED CARBOXYLIC ACID

(71) Applicant: NIPPON KAYAKU KABUSHIKI KAISHA, Tokyo (JP)

(72) Inventors: Ryota Hiraoka, Yamaguchi (JP); Shogo Yasuda, Yamaguchi (JP); Tomoyuki Kawamura, Yamaguchi (JP); Takanori Nakano, Yamaguchi (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/040,677

(22) PCT Filed: Apr. 10, 2019

(86) PCT No.: PCT/JP2019/015660
§ 371 (c)(1),
(2) Date: Sep. 23, 2020

(87) PCT Pub. No.: WO2019/198763
PCT Pub. Date: Oct. 17, 2019

(65) Prior Publication Data
US 2021/0155569 A1 May 27, 2021

(30) Foreign Application Priority Data
Apr. 10, 2018 (JP) .............................. JP2018-075112

(51) Int. Cl.
| | |
|---|---|
| *C07C 45/35* | (2006.01) |
| *C07C 51/00* | (2006.01) |
| *B01J 23/00* | (2006.01) |
| *B01J 23/887* | (2006.01) |
| *C07C 51/235* | (2006.01) |
| *C07C 47/22* | (2006.01) |

(52) U.S. Cl.
CPC ............ *C07C 45/35* (2013.01); *B01J 23/887* (2013.01); *C07C 51/235* (2013.01); *C07C 47/22* (2013.01)

(58) Field of Classification Search
CPC ....... C07C 45/35; C07C 51/235; B01J 23/887
See application file for complete search history.

(56) References Cited

U.S. PATENT DOCUMENTS

| | | | |
|---|---|---|---|
| 5,731,689 A | 3/1998 | Sato | |
| 9,580,376 B2 * | 2/2017 | Kawamura | ............ B01J 23/002 |
| 2002/0007088 A1 | 1/2002 | Tanimoto et al. | |
| 2003/0191344 A1 | 10/2003 | Yunoki | |
| 2015/0274626 A1 | 10/2015 | Yamaguchi et al. | |
| 2016/0059218 A1 | 3/2016 | Nakazawa et al. | |
| 2016/0145180 A1 | 5/2016 | Kawamura et al. | |
| 2018/0029018 A1 | 2/2018 | Kawamura et al. | |

FOREIGN PATENT DOCUMENTS

| | | |
|---|---|---|
| EP | 3 023 406 | 5/2016 |
| JP | 8-336298 | 12/1996 |
| JP | 2001-328951 | 11/2001 |
| JP | 2003-146920 | 5/2003 |
| JP | 2003-164763 | 6/2003 |
| JP | 2004-2209 | 1/2004 |
| JP | 2014-019675 | 2/2014 |
| WO | 2014/073419 | 5/2014 |
| WO | 2014/181839 | 11/2014 |
| WO | 2015/008814 | 1/2015 |
| WO | 2016/136882 | 9/2016 |

OTHER PUBLICATIONS

International Search Report, dated Jun. 25, 2019 in corresponding International Patent Application No. PCT/JP2019/015660, with English language translation.
Japanese Office Action, dated Sep. 10, 2019 in corresponding Japanese Patent Application No. 2019-540018, with English language translation.
Japanese Office Action, dated Nov. 26, 2019 in corresponding Japanese Patent Application No. 2019-540018, with English language translation.
Extended European Search Report dated Nov. 3, 2021 in corresponding European Patent Application No. 19785632.1, 8 pages.

\* cited by examiner

*Primary Examiner* — Sikarl A Witherspoon
(74) *Attorney, Agent, or Firm* — Wenderoth, Lind & Ponack, L.L.P.

(57) ABSTRACT

Provided is a method for producing at least one of an unsaturated aldehyde and an unsaturated carboxylic acid from an alkene by an oxidation reaction, in which a n-layered catalyst layer (n≥2) is provided in a gas flow direction in a reaction tube, two or more kinds of catalysts having different activities are used; and the catalysts are packed in such a manner that dT≤20° C. is satisfied, when a difference between a temperature $PT_n$ of an exothermic peak in a n-th layer as counted from a gas inlet and a minimum value $mT_{n-1}$ of a temperature of a catalyst layer which appears between an exothermic peak in a (n-1)th layer and an exothermic peak in a n-th layer from the gas inlet is represented as dT ($=PT_n-mT_{n-1}$), and the change rate of dT is 2.5 or less at a reaction bath temperature within a range of ±6° C. of a reaction bath temperature at which the highest yield is obtained.

6 Claims, 1 Drawing Sheet

METHOD FOR PRODUCING AT LEAST ONE OF UNSATURATED ALDEHYDE AND UNSATURATED CARBOXYLIC ACID AND CATALYST FOR PRODUCING AT LEAST ONE OF UNSATURATED ALDEHYDE AND UNSATURATED CARBOXYLIC ACID

TECHNICAL FIELD

The present invention relates to a method for producing at least one of a corresponding unsaturated aldehyde and unsaturated carboxylic acid by subjecting an alkene to gas-phase oxidation with molecular oxygen or a molecular oxygen-containing gas in the presence of an oxidation catalyst and a composite metal oxide catalyst used in the method.

BACKGROUND ART

The manufacturing and the production of a catalyst for producing at least one of a corresponding unsaturated aldehyde and unsaturated carboxylic acid using an alkene as a raw material are widely carried out industrially. Among these, many proposals have been made in the related art regarding a catalyst for synthesizing at least one of acrolein and an acrylic acid by subjecting propylene to catalytic gas phase oxidation with molecular oxygen.

In this reaction, the generation of local high temperature parts (hot spots) in a catalyst layer is a serious problem. The generation of hot spots shortens the life of the catalyst, reduces the yield due to an excessive oxidation reaction, and in the worst case leads to a runaway reaction. Therefore, several techniques have been proposed to control the activity of the catalyst filled in a portion where a hot spot is generated, in order to prevent a hot spot temperature.

For example, Patent Document 1 describes a technique of using a catalyst whose activity is adjusted by changing a carrying amount and a calcination temperature. In addition, Patent Document 2 describes a technique of using a catalyst whose activity is adjusted by changing a ratio of an apparent density of the catalyst. Further, Patent Document 3 describes a technique of using a catalyst whose activity is adjusted by changing a content of an inert component of a catalyst molded body, and by changing an occupied volume of the catalyst molded body, the type and/or amount of an alkali metal, and the calcination temperature of the catalyst.

On the other hand, the yield is also important from the industrial viewpoint from the viewpoint of productivity. In particular, many proposals have been made regarding a composition of the catalyst. Among these, Patent Document 4 describes a technique relating to an atomic ratio of iron, cobalt, and nickel. In addition, Patent Document 5 describes a technique relating to an atomic ratio of iron to cobalt and/or nickel. Further, Patent Document 6 describes a technique relating to an atomic ratio of nickel to bismuth, an atomic ratio of nickel to an alkali metal component, and an atomic ratio of bismuth to an alkali metal component, in addition to optimizing the atomic ratio of each element to molybdenum. Further, Patent Document 7 describes an improvement in a composition ratio of bismuth to molybdenum.

Furthermore, Patent Documents 8 and 9 describe an improvement in stable operation in an industrial plant. However, even when the above methods are used for improvement, further improvement of the yield is required in the production of at least one of the corresponding unsaturated aldehyde and unsaturated carboxylic acid by a partial oxidation reaction of the alkene. For example, the yield of a target product influences an amount of the alkene for use in the production and greatly influences the production cost. In addition, since a large amount of by-products are generated by continuing the operation at a low yield, a large burden is applied to a refining step, which causes a problem that the time and operating cost required for the refining step increase. Further, depending on the type of the by-products, the by-products may be deposited on the surface of the catalyst or in a gas flow path near the catalyst. Since the above problems reduce the activity of the catalyst by covering necessary reaction active sites on the surface of the catalyst, it is necessary to forcibly increase the activity and a reaction bath temperature must be raised. Then, the catalyst is subjected to thermal stress, which causes a decrease in life and a further decrease in selectivity, resulting in a decrease in the yield.

RELATED ART

Patent Document

Patent Document 1: JP-A-H08-336298
Patent Document 2: JP-A-2004-002209
Patent Document 3: JP-A-2001-328951
Patent Document 4: JP-A-2003-164763
Patent Document 5: JP-A-2003-146920
Patent Document 6: WO 2014/181839
Patent Document 7: WO 2016/136882
Patent Document 8: JP-A-2014-19675
Patent Document 9: WO 2015/008814

DISCLOSURE OF INVENTION

Problems to be Solved by the Invention

In the industrial plant, there are many factors that cause the reaction to vary, such as the diameter of a reaction tube, the heat removal capacity derived from the structure of a reactor, a heat medium temperature distribution in horizontal and vertical directions, a gas flow velocity distribution in each reaction tube, and a filling degree of the catalyst. Therefore, in the industrial plant, the development of a technique that can be safely and stably maintained at a high yield for a long period of time and that does not have a large influence even when the reaction bath temperature fluctuates is mentioned as an issue.

Although the composition of the catalyst has been improved, a further improvement is still required.

The techniques relating to a stable operation in the related art have the same idea from the viewpoint that a catalyst having a low activity is used as a catalyst near a gas inlet and a catalyst having a high activity is used as a catalyst at a gas outlet.

The applicant of the present application has focused on the fact that the heat of a reaction bath and the heat of reaction generated during the reaction have a large influence on the problems described above, and has found that a more stable plant operation is possible by using a catalyst that generates less heat and that is insensitive to a change in the reaction bath temperature. As a result of diligent examination, the above problems in the industrial plant are solved by controlling the heat generation in the highly active catalyst at the gas outlet to a certain level or less, and reducing the change in an exothermic peak near a reaction bath temperature at which the highest yield is obtained, and the present invention has been completed which can safely and stably maintain a high yield over a long period of time. Further, the generation of reaction by-products due to the heat of reaction is prevented by preventing the influence of the heat of reaction, and the improvement in the yield, that is, the above second problem, is improved.

Means for Solving the Problems

The present invention relates to:

(1) A method for producing at least one of an unsaturated aldehyde and an unsaturated carboxylic acid from an alkene by an oxidation reaction, wherein a n-layered catalyst layer (n≥2) is provided in a gas flow direction in a reaction tube, two or more kinds of catalysts having different activities are used; and the catalysts are packed in such a manner that dT≤20° C. is satisfied, when a difference between a temperature $PT_n$ of an exothermic peak in a n-th layer as counted from a gas inlet and a minimum value $mT_{n-1}$ of a temperature of a catalyst layer which appears between an exothermic peak in a (n−1)th layer and an exothermic peak in a n-th layer from the gas inlet is represented as dT ($=PT_n-mT_{n-1}$), and the change rate of dT is 2.5 or less at a reaction bath temperature within a range of ±6° C. of a reaction bath temperature at which the highest yield is obtained, (2) The method for producing at least one of an unsaturated aldehyde and an unsaturated carboxylic acid according to item (1), wherein at the reaction bath temperature within a range of ±6° C. of the reaction bath temperature at which the highest yield is obtained, at least 10% of the catalysts in each catalyst layer is at a temperature equal to or higher than a temperature for switching of a rate-determining reaction in the oxidation reaction for producing at least one of the unsaturated aldehyde and the unsaturated carboxylic acid from the alkene, (3) The method for producing at least one of an unsaturated aldehyde and an unsaturated carboxylic acid according to item (1) or (2), wherein at the reaction bath temperature within a range of ±6° C. of the reaction bath temperature at which the highest yield is obtained, at least 30% of the catalysts in each catalyst layer is at a temperature equal to or higher than the temperature for switching of the rate-determining reaction in the oxidation reaction, (4) The method for producing at least one of an unsaturated aldehyde and an unsaturated carboxylic acid according to item (2) or (3), wherein a catalyst having a temperature for switching of the rate-determining reaction of 360° C. or lower in the oxidation reaction is used for the n-th catalyst layer, (5) A catalyst for use in the method for producing at least one of an unsaturated aldehyde and an unsaturated carboxylic acid according to any one of items (1) to (4), the catalyst comprising a catalytically active component represented by the following general formula (I):

$$Mo_{12}Bi_aFe_bCo_cNi_dX_eY_fZ_gO_h \qquad \text{General formula (I)}$$

(where X is at least one element selected from the group consisting of magnesium (Mg), calcium (Ca), manganese (Mn), copper (Cu), zinc (Zn), cerium (Ce) and samarium (Sm), Y is at least one element selected from the group consisting of boron (B), phosphorus (P), arsenic (As), antimony (Sb) and tungsten (W), Z is at least one element selected from the group consisting of sodium (Na), potassium (K), rubidium (Rb) and cesium (Cs); a to g represent an atomic ratio of each component; h is a numerical value determined by a degree of oxidation of the catalytically active component; 0.40≤a≤2.0, 1.0≤b≤3.0, 3.0≤c≤9.0, 0.5≤d≤4.0, 0≤e≤10, 0≤f≤10, and 0.01≤g≤0.20 are satisfied; and h is expressed by a numerical value that satisfies oxidation states of the other elements), (6) The catalyst according to item (5), wherein in the catalytically active component, 0.40≤a≤1.3, 1.5≤b≤2.6, 4.0≤c≤7.5, 1.2≤d≤3.5, 0≤e≤10, 0≤f≤10, and 0.02≤g≤0.15 are satisfied in the general formula (I), (7) The catalyst according to item (5) or (6), wherein the atomic ratio of each component of the catalytically active component satisfies the following:

3.0≤(c+d)/(a+b)<4.5

1.0≤((a+b)/(b+c+d))/(g×i)<4.5

(where i represents a Pauling ionic radius of the component Z, and the unit is Å), (8) The catalyst according to item (7), wherein the atomic ratio of each component of the catalytically active component satisfies the following:

3.4≤(c+d)/(a+b)<4.0

1.2≤((a+b)/(b+c+d))/(g×i)<4.0.

(9) The catalyst according to any one of items (5) to (8), wherein a spherical carrier is coated with the catalytically active component, and (10) The catalyst according to any one of items (5) to (9), wherein an average particle diameter of the catalyst (in terms of arithmetic average) is 3.0 mm to 10.0 mm, and a weight of the catalytically active component is 20 to 80% by weight of a total weight of the catalyst.

Effects of the Invention

According to the present invention, it is possible to obtain a catalyst having a high selectivity and a high yield of a target product for producing at least one of a corresponding unsaturated aldehyde and unsaturated carboxylic acid from an alkene, and it is possible to safely and stably maintain a high yield over a long period of time even in an industrial plant.

EMBODIMENTS FOR CARRYING OUT THE INVENTION

Hereinafter, an embodiment of the present invention will be described. In the present embodiment, when producing at least one of a corresponding unsaturated aldehyde and unsaturated carboxylic acid by subjecting an alkene to partial oxidation using a fixed bed multi-tube reactor, if n layered catalyst layers (n≥2) is provided in a gas flow direction in a reaction tube, two or more types of catalysts having different activities are used, and the catalysts are packed such that dT≤20° C. where dT ($=PT_n-mT_{n-1}$) is a difference between a temperature $PT_n$ of an exothermic peak in the n-th layer from a gas inlet and a minimum value $mT_{n-1}$ of a temperature of a catalyst layer between an exothermic peak in the (n−1)th layer and an exothermic peak in the n-th layer, and a change rate of dT is 2.5 or less at a reaction bath temperature within a range of ±6° C. of a reaction bath temperature at which the highest yield is obtained, there is no particular limitation on the catalyst used. In the present embodiment, for example, as the catalyst, a catalyst known per se can be used as long as it is a catalyst used for obtaining at least one of an unsaturated aldehyde and an unsaturated carboxylic acid from an alkene.

The catalyst for used in the present embodiment is preferably a composite metal oxide. In addition, it is more preferable for the catalyst that a temperature for switching of a rate-determining reaction in the oxidation reaction for obtaining at least one of the unsaturated aldehyde and the unsaturated carboxylic acid from the alkene is 360° C. or lower.

Here, regarding the oxidation reaction when using the composite metal oxide, it is known that lattice oxygen contained in the catalyst oxidizes an alkene (for example, propylene) which is a reaction substrate. It is known that, at this time, the rate-determining process differs depending on the reaction temperature, and that an oxygen diffusion rate at a low temperature and a surface reaction rate at a high temperature become rate-determining reactions (Redlingshofer, H., Ind Eng Chem Res., 2003, 42, 5482).

Regarding the switching of the rate-determining reaction, the oxygen diffusion rate is determined by
an adsorption rate of raw material oxygen to [$O_2$—] defects on the surface of the catalyst,
a diffusion rate from the surface of the catalyst to the vicinity of the surface of the catalyst,
a velocity from the vicinity of the surface to the bulk,
a diffusion rate in the bulk,
a velocity from the bulk to the vicinity of the surface,
a velocity from the vicinity of the surface of the catalyst to an active site on the surface of the catalyst, or the like. It is considered that Fe, Co, and Ni, which have the property of rotating a redox cycle in the catalyst, influence the above factors.

Although various models have been proposed for the surface reaction rate, the surface reaction rate is generally determined by
an adsorption rate of the reaction substrate,
a desorption rate of the reaction substrate,
a diffusion rate of the reaction substrate on and the vicinity of the surface of the catalyst,
a diffusion rate in the reaction system, or the like. It is considered that Bi and Fe which have a catalytic reaction point and a reoxidation function after the oxidation reaction, alkali metals which influence acid sites for causing adsorption and desorption, and physical properties such as pores and specific surface area of the catalyst influence the above factors.

As described above, functions which influence the rate-determining reaction are intricately intertwined, and it is not easy to find the relationship thereof. However, the switching of the rate-determining reaction can be experimentally obtained, and the value thereof can be determined by the composition and physical properties.

For example, the value can be determined by evaluating the catalytic activity using a differential type reactor which is generally used for catalyst evaluation and in which heat of reaction in the catalyst layer is not generated as much as possible.

That is, the experimental value is substituted into the general formula (IV) known by the following Arrhenius formula, and a point at which straight lines of the high temperature side and the low temperature side intersect each other is a temperature for switching of the rate-determining reaction.

$$lnk=-(Ea/R)(1/T)+lnA \qquad \text{General formula (IV)}$$

(k represents a reaction rate, Ea represents an activation energy, R represents a gas constant, T represents a reaction temperature, and A represents a frequency factor)

Based on the numerical values obtained in the above experiments, the properties of each rate-determining reaction specific to the catalyst can be defined. Regarding the properties of the rate-determining reaction, various expressions such as the magnitude of activation energy and the magnitude of reaction rate can be used. The expression "temperature for switching of a rate-determining reaction" is useful since it can be understood in relation to the reaction bath temperature in which the catalyst is used, and can be compared with actual observation data.

A preferred range for the temperature for switching of the rate-determining reaction is 310° C. or higher and 360° C. or lower, and more preferably 320° C. or higher and 355° C. or lower. When the temperature for switching of the rate-determining reaction is lower than or equal to the reaction bath temperature, the surface reaction becomes a rate-determining reaction, and it is necessary to increase the surface area in order to carry out a sufficient reaction, which may be difficult in producing the catalyst. When the temperature for switching of the rate-determining reaction is high, in order to obtain a sufficient raw material conversion rate, it is necessary to raise the reaction bath temperature, resulting in a lowered selectivity.

When the temperature for switching of the rate-determining reaction is in a preferred range, the reaction bath temperature can be set low and heat generation due to side reactions can be prevented, so that the temperature of the hot spot generated in the catalyst layer near the gas inlet can be lowered. In addition, it is possible to prevent, in the catalyst layer near the gas outlet, an excessive change in the reaction rate due to a temperature change even at a low reaction bath temperature, so that a stable and long-term operation can be achieved.

The catalyst contained in all catalyst layers of the fixed bed multi-tube reactor for use in the method of the present embodiment is not particularly limited, and preferably contains a composite metal oxide (catalytically active component) having a composition represented by the following general formula (I):

$$Mo_{12}Bi_aFe_bCo_cNi_dX_eY_fZ_gO_h \qquad \text{General formula (I)}$$

(where X is at least one element selected from the group consisting of magnesium (Mg), calcium (Ca), manganese (Mn), copper (Cu), zinc (Zn), cerium (Ce) and samarium (Sm), Y is at least one element selected from the group consisting of boron (B), phosphorus (P), arsenic (As), antimony (Sb) and tungsten (W), Z is at least one element selected from the group consisting of sodium (Na), potassium (K), rubidium (Rb) and cesium (Cs), a to g represent an atomic ratio of each component, h is a numerical value determined by a degree of oxidation of the catalyst component, $0.40 \leq a \leq 2.0$, $1.0 \leq b \leq 3.0$, $3.0 \leq c \leq 9.0$, $0.5 \leq d \leq 4.0$, $0 \leq e \leq 10$, $0 \leq f \leq 10$, $0.01 \leq g \leq 0.20$, and h is expressed by a numerical value that satisfies oxidation states of other elements).

In the general formula (I),
it is more preferable that $0.40 \leq a \leq 1.3$, $1.5 \leq b \leq 2.6$, $4.0 \leq c \leq 7.5$, $1.2 \leq d \leq 3.5$, $0 \leq e \leq 10$, $0 \leq f \leq 10$, and $0.02 \leq g \leq 0.15$.

Here, as a constituent element ratio of the metal element, which is the main component of the catalytically active component, to molybdenum, it is important to make a suitable balance between the ratio of elements involved in the oxygen diffusion rate and the ratio of elements involved in the surface reaction rate. That is, there is a suitable balance depending on the amounts of bismuth and iron, as well as the alkali metal, which influence the surface reaction and the ratio of cobalt to nickel, which influences the redox.

It is preferable that the value calculated by substituting the atomic ratio of each component of the general formula (I) into the following formula (II) falls within a certain range.

[Eq. 1]

$$\frac{c+d}{a+b} \quad \text{Formula (II)}$$

The numerator of the formula (II) is a sum of the composition ratios of cobalt and nickel among the compositions that contribute to the redox cycle, and the denominator is a sum of composition ratios of iron and bismuth that contribute to the surface reaction. That is, the formula (II) is a numerical value expressing the ratio of the metal composition that rotates the redox cycle to the metal composition that contributes to the surface reaction. A preferred range of this value is 3.0 or more and less than 4.5, and more preferably 3.4 or more and less than 4.0.

It is more preferable that the value calculated by substituting the atomic ratio of each component of the general formula (I) into the following formula (III) falls within a certain range.

[Eq. 2]

$$\frac{(a+b)}{(b+c+d) \times (g \times i)} \quad \text{Formula (III)}$$

(In the formula (III), i of the component Z represents a Pauling ionic radius, and the unit is Å).

In the formula (III), the portion represented by $(a+b)/(b+c+d)$ is a value obtained by dividing the sum of the composition ratios of iron and bismuth that contribute to the surface reaction by the sum of the composition ratios of iron, cobalt, and nickel that contribute to the redox cycle, and $(g \times i)$ is a value obtained by multiplying the composition ratio of the alkali metal used by the ionic radius of the alkali metal. That is, the formula (III) is a numerical value expressing the contribution to the surface reaction. A preferred range of this value is 1.0 or more and less than 4.5, and more preferably 1.2 or more and less than 4.0. According to the Pauling ionic radius, sodium is 0.95 Å, potassium is 1.33 Å, rubidium is 1.48 Å, and cesium is 1.69 Å.

The composite metal oxide having the above composition can be prepared, for example, by the following steps, but is not limited to these steps.

Step a): Preparation

In general, starting raw materials of respective elements constituting the catalyst are not particularly limited. As the molybdenum component raw material, molybdenum oxides such as molybdenum trioxide, molybdic acid or salts thereof such as molybdic acid and an ammonium molybdate, molybdenum-containing heteropolyacids or salts thereof such as phosphomolybdic acid and silicomolybdic acid, and the like can be used; however, preferably, in the case of using an ammonium molybdate, a high-performance catalyst can be obtained. In particular, though the ammonium molybdate includes plural kinds of compounds, such as ammonium dimolybdate, ammonium tetramolybdate and ammonium heptamolybdate, among those, the case of using ammonium heptamolybdate is the most preferred. As the bismuth component raw material, bismuth salts such as bismuth nitrate, bismuth subcarbonate, bismuth sulfate and bismuth acetate, bismuth trioxide, metallic bismuth, and the like can be used; however, more preferably, in the case of using bismuth nitrate, a high-performance catalyst can be obtained. As for raw materials of iron, cobalt, nickel, and other elements, oxides, or nitrates, carbonates, organic acid salts, hydroxides, and the like, each of which may become an oxide by strong heat, or mixtures thereof, can be generally used. For example, the iron component raw material and the cobalt component raw material and/or the nickel component raw material are dissolved in a desired ratio in water and mixed under a condition at 10° C. to 80° C.; the mixture is mixed with an aqueous solution or slurry of the separately prepared molybdenum component raw material and Z component raw material under a condition at 20° C. to 90° C.; after heating and stirring the resulting mixture for about 1 hour under a condition at 20° C. to 90° C., an aqueous solution having the bismuth component raw material dissolved therein and optionally the X component raw material and the Y component raw material are added, thereby obtaining an aqueous solution or slurry containing the catalyst components. Hereinafter, both are collectively referred to as a preparation liquid (A). Here, the preparation liquid (A) is not always required to contain all of the catalyst constituent elements, and a part of those elements or a part of the amounts thereof may be added in the sequent step or steps. In addition, on the occasion of preparing the preparation liquid (A), when the amount of water for dissolving each of the component raw materials, or in the case of adding an acid, such as sulfuric acid, nitric acid, hydrochloric acid, tartaric acid, and acetic acid, for the purpose of dissolution, the acid concentration in the aqueous solution sufficient for dissolution of the raw materials is not suitable for the preparation within a range of, for example, 5 to 99% by weight, there would be a case where the form of the preparation liquid (A) is a clay-like lump. In this case, an excellent catalyst is not obtained. The form of the preparation liquid (A) is preferably an aqueous solution or slurry since an excellent catalyst is obtained.

Step b): Drying

Subsequently, the preparation liquid (A) obtained above is dried to form a dry powder. The drying method is not particularly limited so long as it is a method capable of completely drying the preparation liquid (A); however, examples thereof include drum drying, freeze drying, spray drying, evaporation to dryness, and the like. Among these, spray drying in which the slurry can be dried into a powder or granule within a short period of time is particularly preferred in the present embodiment. Although the drying temperature of spray drying varies depending on the concentration of the slurry, the liquid sending speed, or the like, it is approximately 70° C. to 150° C. in terms of a temperature at the outlet of a drying machine. In addition, it is preferable to dry the obtained dry powder such that the most frequent particle diameter thereof is 0.010 μm to 700 μm. More preferably, the most frequent particle diameter thereof is 0.10 μm to 500 μm. Thus, a dry powder (B) is obtained.

Step c): Preliminary Calcination

When the obtained dry powder (B) is subjected to preliminary calcination at 200° C. to 600° C., preferably 300° C. to 600° C. under air circulation, shaping properties, mechanical strength and catalyst performance of the catalyst tend to be improved. The calcination time is preferably 1 to 12 hours. In the preliminary calcination, the performance is adversely influenced when the dry powder obtained in the step b) is sealed and exposed to high temperature in an oxygen-deficient state. Therefore, regarding the air to be circulated, it is preferable to exchange the air on the catalyst at 0.1 m$^3$/min to 200 m$^3$/min, and more preferably 1 m$^3$/min to 100 m$^3$/min. It is preferable to perform the preliminary calcination such that the most frequent particle diameter of a preliminarily calcined powder (C) obtained in the step c) is 0.10 μm to 500 μm. More preferably, the most frequent particle diameter thereof is 1.0 μm to 300 μm.

Step d): Molding

Although the molding method is not particularly limited, on the occasion of shaping in a cylindrical or annular form, a method using a tablet molding machine, an extrusion molding machine, or the like is preferred. The case of shaping in a spherical form is more preferred, and the preliminarily calcined powder (C) may be molded in a spherical form by using a shaping machine; however, a method of carrying the preliminarily calcined powder (C) (including a shaping auxiliary agent and a strength improver, if desired) on a carrier, such as an inert ceramic, is preferred. Here, as for the carrying method, a tumbling granulation method, a method using a centrifugal flow coating apparatus, a wash coating method, and the like are widely known. The carrying method is not particularly limited so long as it is a method capable of uniformly carrying the preliminarily calcined powder (C) on the carrier. However, in the case of taking into account the production efficiency of the catalyst or the performance of the prepared catalyst, more preferably, a method in which using an apparatus having a flat or uneven disk in a bottom of a fixed cylindrical vessel, a carrier charged within the vessel is vigorously agitated by means of rotation motion and revolution motion of the carrier itself by rotating the disk at a high speed, and the preliminarily calcined powder (C) and optionally a shaping auxiliary agent and/or a strength improver, are added thereto, thereby carrying the powder components on the carrier is preferred. It is to be noted that on the occasion of carrying, it is preferred to use a binder. Specific examples of the binder which may be used include water, ethanol, methanol, propanol, a polyhydric alcohol, polyvinyl alcohol that is a polymer-based binder, a silica sol aqueous solution that is an inorganic binder, and the like; ethanol, methanol, propanol, and a polyhydric alcohol are preferred; and a diol such as ethylene glycol, a triol such as glycerin, and the like are more preferred. By using an appropriate amount of a glycerin aqueous solution, the shaping properties become good, and a high-performance catalyst having high mechanical strength is obtained. Specifically, in the case of using an aqueous solution having a glycerin concentration of 5% by weight or more, a catalyst having a particularly high performance is obtained. The use amount of such a binder is typically 2 to 80 parts by weight based on 100 parts by weight of the preliminarily calcined powder (C). As for the inert carrier, a carrier having a diameter of about 2 to 8 mm is generally used, and the preliminarily calcined powder (C) is carried thereon. The carrying rate is determined taking into account a use condition of the catalyst, for example, a reaction condition, such as a space velocity of the reaction raw materials, and raw material concentrations, and is typically 20 to 80% by weight. Here, the carrying rate is expressed according to the following formula.

[Eq. 3]

$$\text{Carrying rate (\% my weight)} = 100 \times \frac{A}{A+B} \quad \text{General formula (V)}$$

In the general formula (V),
A=weight of the preliminarily calcined powder (C) used for shaping
B=weight of the inert carrier used for shaping.

A molded body (D) is obtained by the step d). The mechanical strength of the molded body (D) is also greatly influenced by the atomic ratios of the catalyst composition. That is, the mechanical strength of the molded body (D) is influenced by the kind of a compound to be formed by adjusting the atomic ratios, or the matter that even in the same compound, the phase form of a crystal structure is different. In addition, the diameter of the composite metal oxide particle formed in the preparation step or drying step or the geometric structure of the particle, and the coagulation form thereof change, and therefore, the mechanical strength of the molded body (D) is also influenced by changes in micro physical properties, such as strength of the compound crystal in the composite metal oxide, or macro physical properties, for example, the particle diameter distribution of the preliminarily calcined powder. Overall physical properties including not only the preparation method of each step but also the influence of the atomic ratios determine the mechanical strength of the ultimately prepared catalyst.

Step e): Main Calcination

The molded body (D) tends to have improved catalytic activity and selectivity by calcination at a temperature of 200° C. to 600° C. for about 1 to 12 hours. The calcination temperature is preferably 400° C. or higher and 600° C. or lower, and more preferably 500° C. or higher and 600° C. or lower. Air is simple and easy and preferred as the gas to be circulated; however, besides, as an inert gas, it is also possible to use nitrogen or carbon dioxide, or a nitrogen oxide-containing gas, an ammonia-containing gas, a hydrogen gas, or a mixture thereof for the purpose of rendering the system into a reducing atmosphere. Thus, a catalyst (E) is obtained. In the main calcination, when there is little contact between the gas to be circulated and the molded body (D), there are problems in appearance and performance, such as uneven burning and charring, and the catalyst being in an oxygen-deficient state. In order to avoid such problems, it is necessary to exchange a certain amount of air or more in a calcination furnace, and it is preferable to exchange the air on the catalyst in the range of 0.1 m$^3$/min to 200 m$^3$/min, and more preferably 1 m$^3$/min to 100 m$^3$/min. When the circulation amount is large, the temperature distribution in the calcination furnace may fluctuate, and the calcination temperature cannot be substantially controlled.

Chemical properties and physical properties of the obtained catalyst (E) can be confirmed by various analytical techniques. There are various measurement methods, and examples thereof include confirmation of the crystal structure by X-ray diffraction, measurement of the surface area or pore volume by BET and mercury porosimetry, and measurement of the acid strength and acid amount at the acid site on the surface by the ammonia adsorption method. As described above, the above properties influence the temperature for switching of the rate-determining reaction, and are therefore particularly important.

Particularly in the X-ray diffraction, peaks of composite metal oxides of Bi, Fe, Co, and Ni with Mo are important. In the case of comparing relative intensities of one peak of peaks at diffraction angles 2θ of 14.1°, 25.3°, and 26.4° with another peak as a reference, an increase in the relative intensity of these peaks means an increase in the long repeating structure in the crystal structure, which may improve oxygen transport capacity, and is thus preferred. Therefore, a ratio of the peak intensity of 25.3° or 26.4° to the peak intensity of 14.1° at a temperature equal to or higher than the temperature for switching of the rate-determining reaction is preferably 1.00 times or more, more preferably 1.04 times or more, still more preferably 1.06 times or more, particularly preferably 1.10 times or more, and most preferably 1.18 times or more, as compared with the ratio of the peak intensity at a temperature lower than the temperature for switching of the rate-determining reaction.

In addition, it is industrially necessary that the shape of the obtained catalyst is produced within a certain variation range. When the shape of the catalyst varies greatly, the reaction varies in an industrial plant, which is not preferred. Regarding the particle diameter of the catalyst, for example, the average particle diameter and the standard deviation can be determined by measuring the diameter of the obtained catalyst using a caliper or the like. The amount required for measurement is a statistically dominant number, and sufficiently represents the obtained catalyst. For use in an industrial plant, the average particle diameter of the catalyst is preferably in the range of 3.0 mm to 10.0 mm in terms of arithmetic average. The standard deviation is preferably 5% or less, and more preferably 1% or less of the average particle diameter. When the standard deviation of the particle diameter of the catalyst is large, a variation in the filling in the reaction tube is large, leading to a variation in the reaction in the industrial plant as described above.

The catalytic gas phase oxidation reaction of the alkene in the present embodiment is carried out by introducing a mixed gas composed of 6 to 12% by volume of an alkene, 5 to 18% by volume of molecular oxygen, 0 to 60% by volume of steam, and 20 to 70% by volume of an inert gas, for example, nitrogen and carbon dioxide, in terms of a raw material gas composition onto the catalyst prepared above at a temperature range from 250° C. to 450° C. under a pressure of atmospheric pressure to 10 atms, preferably atmospheric pressure to 5 atms, and more preferably atmospheric pressure to 3 atms for a contact time of 0.5 to 10 seconds. In the present embodiment, the alkene is intended to include alcohols that generate an alkene in an intramolecular dehydration reaction, for example, tertiary butyl alcohol. A higher space velocity (reaction substrate supply rate (NL/hr)/catalyst filling space volume (L)) of the reaction substrate such as an alkene with respect to the volume of the catalyst is preferred from the viewpoint of production efficiency. However, when the space velocity is too high, the yield of the target product (such as acrolein or an acrylic acid) may decrease, and the life of the catalyst may be shortened. Therefore, in practice, the space velocity is preferably in the range of 40 to 200 $hr^{-1}$, and more preferably 60 to 180 $hr^{-1}$. Here, NL represents the volume of the reaction substrate in the standard state. The conversion rate of the alkene is generally 85.0 mol % to 99.5 mol %, preferably 90.0 mol % to 99.0 mol %, and more preferably 93.0 mol % to 98.0 mol % when the target product is acrolein. In addition, the conversion rate is preferably around a high effective yield (yield of acrolein+yield of acrylic acid), generally 90.0 mol % to 99.9 mol %, preferably 95.0 mol % to 99.5 mol %, and more preferably 97.0 mol % to 99.0 mol %, when the target product is both acrolein and an acrylic acid. In the present embodiment, when the reaction at a lower temperature is used for the suitable acrolein production, the greatest effect can be obtained.

In the present embodiment, it is preferable to provide a plurality of catalyst layers in the reaction tube in the raw material gas flow direction, and it is more preferable to dispose a plurality of catalysts having different activities to make the activity become higher from the raw material inlet toward the outlet in the raw material gas flow direction. The number of divisions is not particularly limited, but is generally 2 to 5, and preferably 2 to 3. In the plurality of catalyst layers, there is an exothermic peak (a point at which the temperature has a maximum value at the observation point of one catalyst layer) for each layer, and as a result, at least two or more exothermic peaks are observed in the reaction tube. When there is one exothermic peak in the reaction tube, for example, when there is an exothermic peak only in the catalyst layer at the raw material inlet, if the conversion rate of the raw material is low and there is an exothermic peak only in the catalyst layer at the outlet, the selectivity of the target product is poor.

In the present embodiment, the catalyst layer may be composed of only the catalyst or a mixture of the catalyst and the inert carrier.

When the catalyst and the inert carrier are mixed, the activity of the catalyst can be adjusted. As the inert carrier, a carrier having no catalytic activity such as silica alumina can be used.

According to the production method of the present embodiment, it is possible to maintain safe, stable and high yield for long period of time in the industrial plant, and it is possible to produce at least one of the unsaturated aldehyde and unsaturated carboxylic acid from the alkene without significantly influencing the yield even when the reaction bath temperature fluctuates.

It is preferable to use an actually measured temperature as the temperature required for obtaining the value of dT or the like. To measure the temperature of the catalyst layer, a thermocouple is installed in the reaction tube in the gas flow direction, and the temperature is measured at an interval of 5 cm to 10 cm. A smaller temperature measurement interval is preferred, and an interval larger than 10 cm is not preferred since accurate data may not be obtained.

In the obtained temperature distribution, the point at which the temperature in each catalyst layer reaches a maximum value is the exothermic peak, and the temperature of the exothermic peak in the n-th layer is described as $PT_n$. In addition, the minimum value of the temperature of the catalyst layer between the exothermic peak in the (n−1)th layer and the exothermic peak in the n-th layer from the gas inlet is described as $mT_{n-1}$. Further, in the present embodiment, the point at which the temperature of the highest exothermic peak is observed in the entire catalyst divided into n layers for reaction is defined as a hot spot. Generally, the catalyst at the gas outlet is filled with a highly active catalyst, but when the catalyst layer is provided such that dT ($=PT_n-mT_{n-1}$) is 20° C. or lower, the raw material can be converted to the target product with a higher selectivity. dT is more preferably 18° C. or lower.

Even when the reaction bath temperature is not intentionally changed in the industrial plant, the reaction bath temperature may slightly fluctuate due to the influence of disturbance external factors. Examples of the disturbance external factors include a change in the flow rate of the heat medium supplied into the reaction bath jacket of the reactor or a fluctuation in the flow rate of the raw material gas due to a change in the outside air temperature. Due to these influences, a stable operation is difficult in the industrial plant. However, when a change in dT near the reaction bath temperature at which the target product is most obtained is prevented, a stable operation can be realized. The expression "near the reaction bath temperature" means within ±5° C.°, and more preferably within ±10° C.° of the reaction bath temperature. The change rate of dT in the above temperature range is obtained, and this change rate is preferably kept to 2.5 or less, and more preferably 2.0 or less. Here, the "change rate of dT" is obtained by dividing the amount of change in dT in the case of changing the reaction bath temperature by the change temperature in the reaction bath temperature. The change rate of dT can be kept to 2.5 or less, and more preferably 2.0 or less within ±6° C., more preferably within ±5° C., still more preferably within ±4° C., and particularly preferably within ±3° C. with respect to the reaction bath temperature of the UYmax (a point at which the effective yield is the highest). In the case of using the present embodiment a method for producing acrolein, when the reference UYmax is changed, the change rate of dT within ±6° C., preferably ±5° C., more preferably ±4° C., and particularly preferably within ±3° C. is used with the reaction bath temperature of ACRLmax (the point at which the effective yield of acrolein is highest) as a reference.

In each catalyst layer, when a certain proportion or more of the catalyst is used at a temperature equal to or higher than the temperature for switching of the rate-determining reaction the catalyst performance can be sufficiently exhibited. This proportion can be calculated based on the temperature distribution obtained under the reaction bath temperature kept constant. For example, a method of integrating areas sandwiched between respective layers in the temperature distribution and the temperature for switching of the rate-determining reaction, and a method of confirming whether each measurement point is at a temperature equal to or higher than the temperature for switching of the rate-determining reaction, and then dividing the value obtained by multiplying the measurement interval by the number of measurement points at a temperature equal to or higher than the temperature for switching of the rate-determining reaction by the filling length can be appropriately adopted. In the present embodiment, it is confirmed whether the measured temperature of the thermocouple is at a temperature equal to or higher than the temperature for switching of the rate-determining reaction, and the value obtained by multiplying the measurement interval by the number of measurement points at a temperature equal to or higher than the temperature for switching of the rate-determining reaction is divided by the filling length. When this proportion is a certain value or less, the conversion rate of the raw material is remarkably reduced, and a stable operation cannot be performed. Preferably, the operation is performed such that 10% or more of the catalyst is used at a temperature equal to or higher than the temperature for switching of the rate-determining reaction, and more preferably, when 30% or more of the catalyst is used, a stable operation can be performed.

EXAMPLES

Hereinafter, Examples will be shown with specific examples, the present invention is not limited to Examples without departing from the spirit thereof.

In the following, the definitions of the yield of acrolein, the yield of acrylic acid, and useful yield are as follows.

[Eq. 4]

$$\text{Yield of acrolein (mol \%)} = \frac{\text{molar amount of generated acrolein}}{\text{molar amount of supplied propylene}} \times 100$$

$$\text{Yield of acrylic acid (mol \%)} = \frac{\text{molar amount of generated acrylic acid}}{\text{molar amount of supplied propylene}} \times 100$$

Effective yield (mol %) = yield of acrolein + yield of acrylic acid

Catalyst Production Example 1

800 parts by weight of ammonium heptamolybdate tetrahydrate was completely dissolved in 3040 parts by weight of pure water warmed to 60° C. Subsequently, 3.68 parts by weight of cesium nitrate was dissolved in 33 ml of pure water and added to the above solution. Subsequently, 305.1 parts by weight of ferric nitrate nonahydrate, 714.4 parts by weight of cobalt nitrate hexahydrate, and 274.5 parts by weight of nickel nitrate hexahydrate were dissolved in 686 ml of pure water warmed to 60° C. These solutions were gradually mixed while stirring. Subsequently, a solution prepared by completely dissolving 183.2 parts by weight of bismuth nitrate to a nitric acid aqueous solution, prepared by adding 46.6 parts by weight of nitric acid (60% by weight) to 194 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 540° C. for 4 hours, thereby obtaining a Spherical Catalyst A of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst A was Mo:Bi:Fe:Co:Ni:Cs=12:1.0:2.0:6.5:2.5:0.05. When substituting the atomic ratio into the formulas (II) and (III), formula (II)=3.0, and formula (III)=3.2.

The temperature for switching of the rate-determining reaction of the catalyst was 350.1° C.

Regarding the X-ray diffraction peak (peak intensity at 25.3°/peak intensity at 14.1°), the value obtained by dividing the value at 400° C. (equal to or higher than the temperature for switching of the rate-determining reaction) by the value at 30° C. (lower than temperature for switching of the rate-determining reaction) was 1.05.

Catalyst Production Example 2

800 parts by weight of ammonium heptamolybdate tetrahydrate was completely dissolved in 3040 parts by weight of pure water warmed to 60° C. Subsequently, 2.92 parts by weight of potassium nitrate was dissolved in 30 ml of pure water and added to the above solution. Subsequently, 305.1 parts by weight of ferric nitrate nonahydrate, 769.4 parts by weight of cobalt nitrate hexahydrate, and 274.5 parts by weight of nickel nitrate hexahydrate were dissolved in 715 ml of pure water warmed to 60° C. These solutions were gradually mixed while stirring. Subsequently, a solution prepared by completely dissolving 128.2 parts by weight of bismuth nitrate to a nitric acid aqueous solution, prepared by adding 32.6 parts by weight of nitric acid (60% by weight) to 136 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 530° C. for 4 hours, thereby obtaining a Spherical Catalyst B of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst B was Mo:Bi:Fe:Co:Ni:K=12:0.7:2.0:7.0:2.5:0.08. When substituting the atomic ratio into the formulas (II) and (III), formula (II)=3.5, and formula (III)=2.2.

The temperature for switching of the rate-determining reaction of the obtained catalyst B was 348.8° C.

Regarding the X-ray diffraction peak (peak intensity at 25.3°/peak intensity at 14.1°), the value obtained by dividing the value at 400° C. (equal to or higher than the temperature for switching of the rate-determining reaction) by the value at 30° C. (lower than temperature for switching of the rate-determining reaction) was 1.19.

Catalyst Production Example 3

800 parts by weight of ammonium heptamolybdate tetrahydrate was completely dissolved in 3040 parts by weight of pure water warmed to 60° C. Subsequently, 1.40 parts by weight of potassium nitrate was dissolved in 13 ml of pure water and added to the above solution. Subsequently, 305.1 parts by weight of ferric nitrate nonahydrate, 714.4 parts by weight of cobalt nitrate hexahydrate, and 274.5 parts by weight of nickel nitrate hexahydrate were dissolved in 686 ml of pure water warmed to 60° C. These solutions were gradually mixed while stirring. Subsequently, a solution prepared by completely dissolving 183.2 parts by weight of bismuth nitrate to a nitric acid aqueous solution, prepared by adding 46.6 parts by weight of nitric acid (60% by weight) to 194 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 550° C. for 4 hours, thereby obtaining a Spherical Catalyst C of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst C was Mo:Bi:Fe:Co:Ni:K=12:1.0:2.0:6.5:2.5:0.04. When substituting the atomic ratio into the formulas (II) and (III), formula (II)=3.0, and formula (III)=5.1.

The temperature for switching of the rate-determining reaction of the obtained catalyst C was 360.4° C.

Regarding the X-ray diffraction peak (peak intensity at 25.3°/peak intensity at 14.1°), the value obtained by dividing the value at 400° C. (equal to or higher than the temperature for switching of the rate-determining reaction) by the value at 30° C. (lower than temperature for switching of the rate-determining reaction) was 0.98.

Catalyst Production Example 4

800 parts by weight of ammonium heptamolybdate tetrahydrate was completely dissolved in 3040 parts by weight of pure water warmed to 60° C. Subsequently, 1.40 parts by weight of potassium nitrate was dissolved in 13 ml of pure water and added to the above solution. Subsequently, 305.1 parts by weight of ferric nitrate nonahydrate, 714.4 parts by weight of cobalt nitrate hexahydrate, and 274.5 parts by weight of nickel nitrate hexahydrate were dissolved in 686 ml of pure water warmed to 60° C. These solutions were gradually mixed while stirring. Subsequently, a solution prepared by completely dissolving 128.2 parts by weight of bismuth nitrate to a nitric acid aqueous solution, prepared by adding 32.6 parts by weight of nitric acid (60% by weight) to 136 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.0 mm by using a 30% by weight glycerin solution as a binder by a tumbling granulation method. Subsequently, calcination was carried out at a maximum temperature of 540° C. for 4 hours, thereby obtaining a Spherical Catalyst D of the present invention having an average particle diameter of 4.7 mm. The catalytically active component of the catalyst calculated from the charged raw materials was found to be a composite metal oxide having the following atomic ratio.

The atomic ratio of the catalytically active component of the Spherical Catalyst D was Mo:Bi:Fe:Co:Ni:K=12:0.7:2.0:6.5:2.5:0.04. When substituting the atomic ratio into the formulas (II) and (III), formula (II)=3.3, and formula (III)=4.6.

The temperature for switching of the rate-determining reaction of the obtained catalyst D was 359.6° C.

Catalyst Production Example 5

800 parts by weight of ammonium heptamolybdate tetrahydrate was completely dissolved in 3040 parts by weight of pure water warmed to 60° C. Subsequently, 1.40 parts by weight of potassium nitrate was dissolved in 13 ml of pure water and added to the above solution. Subsequently, 305.1 parts by weight of ferric nitrate nonahydrate, 714.4 parts by weight of cobalt nitrate hexahydrate, and 274.5 parts by weight of nickel nitrate hexahydrate were dissolved in 686 ml of pure water warmed to 60° C. These solutions were gradually mixed while stirring. Subsequently, a solution prepared by completely dissolving 128.2 parts by weight of bismuth nitrate to a nitric acid aqueous solution, prepared by adding 32.6 parts by weight of nitric acid (60% by weight) to 136 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 540° C. for 4 hours, thereby obtaining a Spherical Catalyst E of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst E was Mo:Bi:Fe:Co:Ni:K=12:0.7:2.0:6.5:2.5:0.10. When substituting the atomic ratio into the formulas (II) and (III), formula (II)=3.3, and formula (III)=1.8.

The temperature for switching of the rate-determining reaction of the obtained catalyst E was 357.5° C.

Catalyst Production Example 6

800 parts by weight of ammonium heptamolybdate tetrahydrate was completely dissolved in 3040 parts by weight of pure water warmed to 60° C. Subsequently, 5.59 parts by weight of potassium nitrate was dissolved in 55 ml of pure water and added to the above solution. Subsequently, 274.6 parts by weight of ferric nitrate nonahydrate, 571.5 parts by weight of cobalt nitrate hexahydrate, and 307.4 parts by weight of nickel nitrate hexahydrate were dissolved in 611 ml of pure water warmed to 60° C. These solutions were gradually mixed while stirring. Subsequently, a solution prepared by completely dissolving 311.4 parts by weight of bismuth nitrate in a nitric acid aqueous solution, prepared by adding 79.3 parts by weight of nitric acid (60% by weight) to 330 ml of pure water, was added to the above solution and mixed with stirring. This slurry was dried by a disc type spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 560° C. for 4 hours, thereby obtaining a Spherical Catalyst F of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst F was Mo:Bi:Fe:Co:Ni:K=12:1.7:2.0:5.2:2.8:0.15. When substituting the atomic ratio into the formulas (II) and (III), formula (II)=2.2, and formula (III)=1.9.

The temperature for switching of the rate-determining reaction of the obtained catalyst F was 352.2° C.

Catalyst Production Example 7

800 parts by weight of ammonium heptamolybdate tetrahydrate was completely dissolved in 3040 parts by weight of pure water warmed to 60° C. Subsequently, 2.78 parts by weight of rubidium nitrate was dissolved in 25 ml of pure water and added to the above solution. Subsequently, 305.1 parts by weight of ferric nitrate nonahydrate, 714.4 parts by weight of cobalt nitrate hexahydrate, and 274.5 parts by weight of nickel nitrate hexahydrate were dissolved in 686 ml of pure water warmed to 60° C. These solutions were gradually mixed while stirring. Subsequently, a solution prepared by completely dissolving 128.2 parts by weight of bismuth nitrate to a nitric acid aqueous solution, prepared by adding 32.6 parts by weight of nitric acid (60% by weight) to 136 ml of pure water, was added to the above solution and mixed with stirring. This slurry was dried by a spray drying method, and the obtained dry powder was subjected to preliminary calcination at a maximum temperature 440° C. for 4 hours. Crystalline cellulose was added in a proportion of 5% by weight relative to the preliminarily calcined powder and thoroughly mixed. Subsequently, the mixture was carried and molded in a spherical form at a carrying rate of 50% by weight on an inert spherical carrier having an average particle diameter of 4.5 mm by using a 30% by weight glycerin solution as a binder by a tumbling granulation method. Subsequently, calcination was carried out at a maximum temperature of 550° C. for 4 hours, thereby obtaining a Spherical Catalyst G of the present invention having an average particle diameter of 5.2 mm. The catalytically active component of the catalyst calculated from the charged raw materials was found to be a composite metal oxide having the following atomic ratio.

The atomic ratio of the catalytically active component of the Spherical Catalyst G was Mo:Bi:Fe:Co:Ni:Rb=12:0.7:2.0:6.5:2.5:0.05. When substituting the atomic ratio into the formulas (II) and (III), formula (II)=3.3, and formula (III)=3.3.

The temperature for switching of the rate-determining reaction of the obtained catalyst G was 351.0° C.

Example 1

An oxidation reaction of propylene was carried out by using the catalyst A and the catalyst B prepared in Catalyst Production Examples 1 and 2. A jacket for circulating a molten salt as a heat medium and a thermocouple for measuring the temperature of the catalyst layer were installed in a stainless steel reactor having an inner diameter of 25 mm on the tube axis at an interval of 5 cm, and a catalyst layer was provided from the raw material gas inlet side toward the raw material gas outlet of the stainless steel reactor in the following manner. A catalyst layer having a three-layer structure was obtained by filling 80 cm of a diluted catalyst obtained by mixing the catalyst A and a silica-alumina mixture as an inert spherical carrier at a weight ratio of 85:15 as the first catalyst layer (raw material gas inlet side), filling 80 cm of the catalyst A as the second catalyst layer, and filling 190 cm of the catalyst B as the third catalyst layer.

Figure 1:
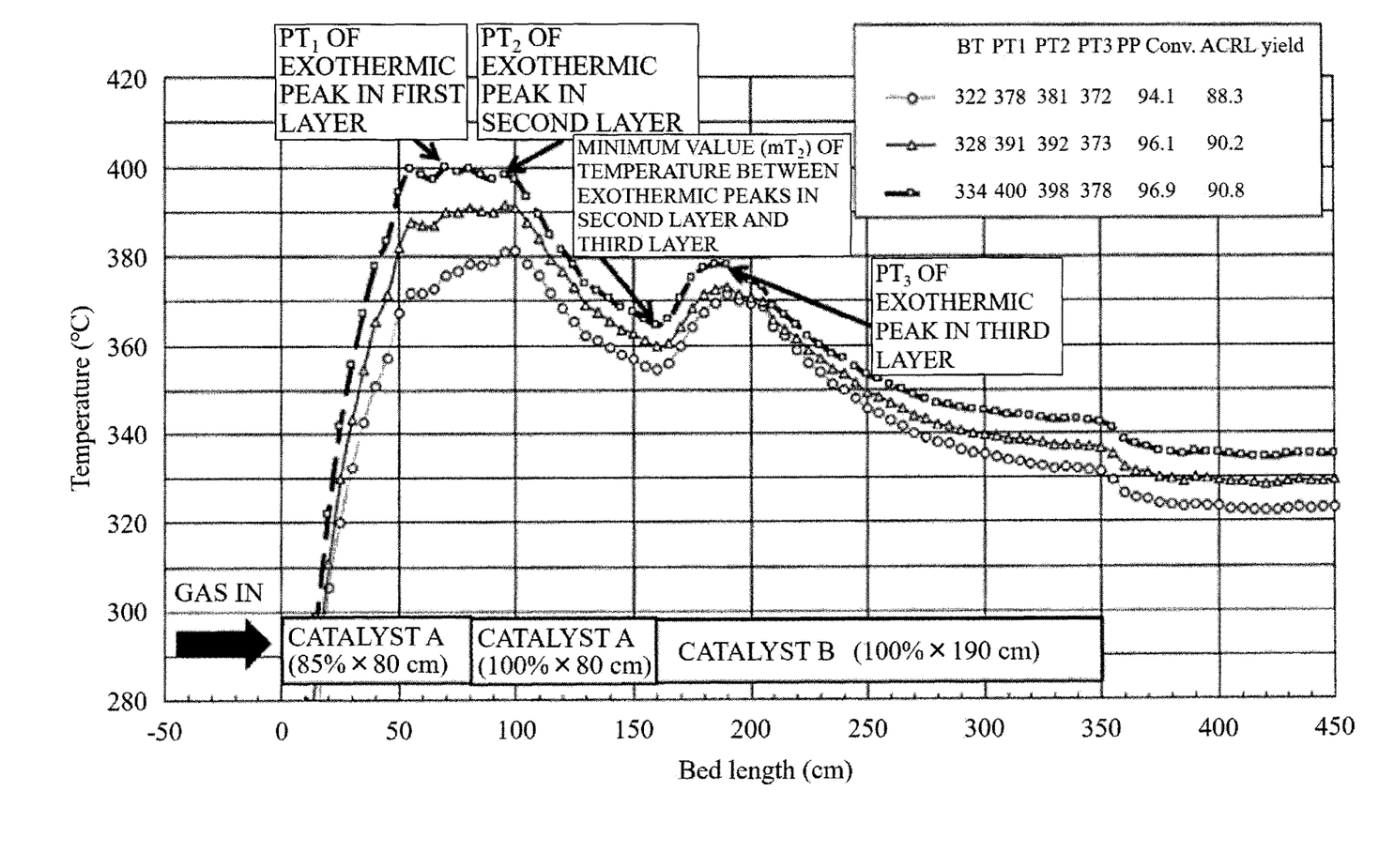
FIG. 1 is a graph showing results of Example 1. The vertical axis represents a temperature of a catalyst layer, and the horizontal axis represents a length of a reaction tube. □ represents a temperature transition of the catalyst layer when a reaction bath temperature (BT) is 334° C., Δ is a temperature transition of the catalyst layer when the reaction bath temperature (BT) is 328° C., and ○ is a temperature transition of the catalyst layer when the reaction bath temperature (BT) is 322° C.

Here, the oxidation reaction of propylene was carried out by setting supply amounts of propylene, air, water and nitrogen to be propylene:oxygen:water:nitrogen=1:1.7:1.0:8.8 as a raw material molar ratio, circulating propylene at a space velocity of 150 hr$^{-1}$, setting the pressure on the outlet side of the reaction tube during the entire gas circulation to 80 kPaG for 200 hours or longer after starting the reaction, and then changing the reaction bath temperature. The reaction bath temperature was changed in the range of 315° C. to 345° C. to obtain the temperature at which the yield of acrolein was maximized (ACRLmax). Table 1 showed results of a reaction result at the reaction bath temperature in near the above temperature, the exothermic peak ($PT_n$) of each catalyst layer at that time, the minimum value ($mT_{n-1}$) of the temperature of the catalyst layer between the exothermic peak in the (n−1)th layer and the exothermic peak in the n-th layer, dT, the change rate of dT, and the proportion of the catalyst having a temperature equal to or higher than the temperature for switching of the rate-determining reaction. FIG. 1 shows measurement results of the temperature of the catalyst layer. FIG. 1 shows the temperature ($PT_1$) of the exothermic peak in the first catalyst layer, the temperature ($PT_2$) of the exothermic peak in the second catalyst layer, the temperature ($PT_3$) of the exothermic peak in the third catalyst layer, and the minimum value ($mT_2$) of the temperature of the catalyst layer observed between the exothermic peak in the second catalyst layer and the exothermic peak in the third catalyst layer when the reaction bath temperature (BT) was 334° C. (□).

Comparative Example 1

A catalyst layer was obtained in the same manner as in Example 1 except that the catalyst C was used instead of the catalyst B. The results were shown in Table 1.

Example 2

The carrier used for the catalyst A and the catalyst B was changed to a carrier having an average particle diameter of 4.0 mm to obtain a catalyst A' and a catalyst B' each having an average particle diameter of 4.7 mm, and a catalyst layer having a two-layer structure was obtained by filling 200 cm of the catalyst A' as the first catalyst layer and filling 150 cm of the catalyst B' as the second catalyst layer in order from the raw material gas inlet side toward the raw material gas outlet of a stainless steel reactor having an inner diameter of 22 mm. The oxidation reaction of propylene was carried out in the same manner as in Example 1 except that the supply amounts of propylene, air, water, and nitrogen was set to be propylene:oxygen:water:nitrogen=1:2.0:0.5:12.0 as a raw material molar ratio, and the space velocity of propylene was 160 hr$^{-1}$. The results were shown in Table 1.

Example 3

Example 3 was the same as Example 2 except that the carrying rate of the catalyst A was 40% (catalyst A"), the catalyst D was used, and a catalyst layer having a two-layer structure was obtained by filling 200 cm of the catalyst A" as the first catalyst layer and filling 150 cm of the catalyst D as the second catalyst layer. The results were shown in Table 1.

Example 4

The carrier used for the catalyst D was changed to a carrier having an average particle diameter of 4.5 mm to obtain a catalyst D' having an average particle diameter of 5.2 mm, and a catalyst layer having a two-layer structure was obtained by filling 100 cm of the catalyst E as the first catalyst layer and filling 250 cm of the catalyst D' as the second catalyst layer. The oxidation reaction of propylene was carried out in the same manner as in Example 1 except that the supply amounts of propylene, air, water, and nitrogen was set to be propylene:oxygen:water:nitrogen=1:1.7:3.0:7.0 as a raw material molar ratio, the space velocity of propylene was 120 hr$^{-1}$, and the pressure on the outlet side of the reaction tube was set to 30 kPaG. The results were shown in Table 1.

Example 5

Under the same conditions as in Example 1, the temperature (UYmax) at which the effective yield (acrolein+acrylic acid) was maximized was obtained. Table 2 showed results of a reaction result at the reaction bath temperature in near the above temperature, the exothermic peak ($PT_n$) of each catalyst layer at that time, the minimum value ($mT_{n-1}$) of the temperature of the catalyst layer between the exothermic peak in the (n−1)th layer and the exothermic peak in the n-th layer, dT, the change rate of dT, and the proportion of the catalyst having a temperature equal to or higher than the temperature for switching of the rate-determining reaction.

Comparative Example 2

Comparative Example 2 was the same as Example 5 except that the catalyst C was used instead of the catalyst B. The results were shown in Table 2.

Example 6

The carrier used for the catalyst A was changed to a carrier having an average particle diameter of 6.0 mm to obtain a catalyst A''' having an average particle diameter of 7.1 mm, and a catalyst layer having a two-layer structure was obtained by filling 100 cm of the catalyst A''' as the first catalyst layer and filling 200 cm of the catalyst D as the second catalyst layer in order from the raw material gas inlet side toward the raw material gas outlet of a stainless steel reactor having an inner diameter of 27 mm. The oxidation reaction of propylene was carried out in the same manner as in Example 5 except that the supply amounts of propylene, air, water, and nitrogen was set to be propylene:oxygen:water:nitrogen=1:1.8:2.0:7.5 as a raw material molar ratio, and the space velocity of propylene was 140 hr$^{-1}$. The results were shown in Table 2.

Example 7

Example 7 was the same as Example 6 except that the carrier used for the catalyst E was changed to a carrier having an average particle diameter of 6.0 mm to obtain a catalyst E having an average particle diameter of 7.1 mm, and a catalyst layer having a two-layer structure was obtained by filling 100 cm of the catalyst E as the first catalyst layer and filling 200 cm of the catalyst D as the second catalyst layer. The results were shown in Table 2.

Comparative Example 3

Comparative Example 3 was the same as Example 6 except that a catalyst layer having a two-layer structure was obtained by filling 100 cm of the catalyst A as the first catalyst layer and filling 200 cm of the catalyst C as the second catalyst layer. The results were shown in Table 2.

Example 8

A catalyst layer having a two-layer structure was obtained in the same manner as in Example 6 except that 100 cm of the catalyst A was filled as the first catalyst layer, and 200 cm of the catalyst D was filled as the second catalyst layer. The oxidation reaction of propylene was carried out in the same manner as in Example 6 except that the space velocity of propylene was set to 100 hr$^{-1}$. The results were shown in Table 2.

Comparative Example 4

Comparative Example 4 was the same as Example 8 except that a catalyst layer having a two-layer structure was obtained by filling 100 cm of the catalyst F as the first catalyst layer and filling 200 cm of the catalyst C as the second catalyst layer. The results were shown in Table 2.

Example 9

A catalyst layer having a two-layer structure was obtained by filling 150 cm of the catalyst E as the first catalyst layer and filling 300 cm of the catalyst D as the second catalyst layer in order from the raw material gas inlet side toward the raw material gas outlet of a stainless steel reactor having an inner diameter of 22 mm. The oxidation reaction of propylene was carried out in the same manner as in Example 5 except that the supply amounts of propylene, air, water, and nitrogen was set to be propylene:oxygen:water:nitrogen=1: 1.9:4.0:7.5 as a raw material molar ratio, and the space velocity of propylene was 130 hr$^{-1}$. The results were shown in Table 2.

Example 10

Example 10 was the same as Example 9 except that the carrier used for the catalyst F was changed to a carrier having an average particle diameter of 4.0 mm to obtain a catalyst F' having an average particle diameter of 4.7 mm, and a catalyst layer having a two-layer structure was obtained by filling 150 cm of the catalyst F' as the first catalyst layer and filling 300 cm of the catalyst D as the second catalyst layer. The results were shown in Table 2.

Example 11

Example 11 was the same as Example 9 except that the carrier used for the catalyst D was changed to a carrier having an average particle diameter of 4.5 mm to obtain a catalyst D' having an average particle diameter of 5.2 mm, and a catalyst layer having a two-layer structure was obtained by filling 150 cm of the catalyst Gas the first catalyst layer and filling 300 cm of the catalyst D' as the second catalyst layer. The results were shown in Table 2.

The results of the above Examples and Comparative Examples are summarized. It can be seen from Table 1 that the present invention in which dT≤20° C. and the change rate of dT is 2.5 or less is suitable for acrolein production. For example, it can be seen in Example 1 that, due to the change in the reaction bath temperature, the change in the conversion rate of propylene is 2.8%, and the change in the yield of acrolein is 0.7%. On the other hand, In Comparative Example 2 in which the reaction is carried out under the same conditions, the change in the conversion rate of propylene is 6.3% and the change in the yield of acrolein is 3.5%, which is high. That is, it is confirmed that a stable catalyst package that is not easily influenced by the temperature change of the reaction bath temperature can be provided.

It can also be confirmed in Table 2 that the present invention is particularly suitable in the first stage for producing an acrylic acid. For example, in Example 5, the yield is 91.2%, and the conversion rate of propylene and the change rate of dT are stable. On the other hand, In Comparative Example 2, the change rate of dT is 2.5 or less and is stable, but dT is high, and the yield cannot be said to be sufficient.

Further, in the comparison between Examples 6 and 7 and Comparative Example 3 in Table 2, as in the case between Example 1 and Comparative Example 1 described above, there is a large difference in stability due to the reaction bath temperature.

TABLE 1

| | | | | | | | | | | Proportion (%) of catalyst having temperature equal to or higher than temperature for switching of rate-determining reaction | | |
|---|---|---|---|---|---|---|---|---|---|---|---|---|
| | Reaction bath temperature (° C.) | PT$_1$ (° C.) | PT$_2$ (° C.) | PT$_3$ (° C.) | mT$_{n-1}$ (° C.) | Conversion rate of propylene (%) | Yield of acrolein (%) | dT (° C.) | Change rate of dT | First layer | Second layer | Third layer |
| Example 1 | 328 | 391.1 | 391.5 | 373.2 | 359.7 | 96.1 | 83.2 | 13.5 | — | 56 | 100 | 45 |
| | 322 | 378.3 | 381.2 | 371.5 | 354.4 | 94.1 | 82.6 | 17.1 | 0.06 | 50 | 100 | 39 |
| | 334 | 399.8 | 398.1 | 378.0 | 364.5 | 96.9 | 82.5 | 13.5 | 0.00 | 63 | 100 | 53 |

TABLE 1-continued

Experiment results (ACRLmax)

| | Reaction bath temperature (°C.) | $PT_1$ (°C.) | $PT_2$ (°C.) | $PT_3$ (°C.) | $mT_{n-1}$ (°C.) | Conversion rate of propylene (%) | Yield of acrolein (%) | dT (°C.) | Change rate of dT | Proportion (%) of catalyst having temperature equal to or higher than temperature for switching of rate-determining reaction | | |
|---|---|---|---|---|---|---|---|---|---|---|---|---|
| | | | | | | | | | | First layer | Second layer | Third layer |
| Comparative Example 1 | 327 | 387.5 | 388.6 | 369.7 | 360.3 | 95.6 | 82.3 | 9.4 | — | 56 | 100 | 29 |
| | 324 | 381.4 | 383.7 | 358.2 | 357.1 | 89.3 | 78.8 | 1.1 | 2.77 | 50 | 100 | 0 |
| | 330 | 392.0 | 393.0 | 382.5 | 363.8 | 96.6 | 81.9 | 18.7 | 3.10 | 56 | 100 | 29 |
| Example 2 | 331 | 379.4 | 355.0 | — | 338.0 | 95.8 | 84.0 | 17.0 | — | 30 | 37 | — |
| | 328 | 375.0 | 352.0 | — | 335.0 | 95.2 | 84.0 | 17.0 | 0.00 | 28 | 27 | — |
| | 334 | 383.0 | 358.0 | — | 340.9 | 96.3 | 83.9 | 17.1 | −0.03 | 33 | 47 | — |
| Example 3 | 335 | 387.4 | 367.6 | — | 350.5 | 96.0 | 83.8 | 17.1 | — | 95 | 33 | — |
| | 331 | 380.4 | 363.6 | — | 347.0 | 94.7 | 83.4 | 16.6 | 0.13 | 75 | 20 | — |
| | 338 | 393.1 | 370.8 | — | 353.4 | 96.7 | 83.7 | 17.4 | 0.10 | 98 | 40 | — |
| Example 4 | 322 | 409.7 | 354.9 | — | 347.7 | 96.8 | 83.9 | 7.2 | — | 70 | 0 | — |
| | 319 | 400.6 | 350.3 | — | 345.1 | 95.4 | 83.4 | 5.2 | −0.67 | 60 | 0 | — |
| | 325 | 415.0 | 357.2 | — | 349.7 | 97.6 | 83.4 | 7.5 | −0.10 | 75 | 0 | — |

TABLE 2

Experiment results (UYmax)

| | Reaction bath temperature (°C.) | $PT_1$ (°C.) | $PT_2$ (°C.) | $PT_3$ (°C.) | $mT_{n-1}$ (°C.) | Conversion rate of propylene (%) | UY (%) | dT (°C.) | Change rate of dT | Proportion (%) of catalyst having temperature equal to or higher than temperature for switching of rate-determining reaction | | |
|---|---|---|---|---|---|---|---|---|---|---|---|---|
| | | | | | | | | | | First layer | Second layer | Third layer |
| Example 5 | 340 | 411.2 | 406.0 | 383.0 | 369.8 | 97.6 | 91.2 | 13.2 | — | 69 | 100 | 89 |
| | 334 | 399.8 | 398.1 | 378.0 | 364.5 | 96.9 | 90.8 | 13.5 | 0.05 | 63 | 100 | 53 |
| | 343 | 416.7 | 410.3 | 385.6 | 372.8 | 97.9 | 91.1 | 12.8 | 0.13 | 69 | 100 | 100 |
| Comparative Example 2 | 339 | 407.5 | 405.3 | 393.1 | 371.7 | 98.0 | 90.9 | 21.4 | — | 63 | 100 | 34 |
| | 333 | 397.7 | 397.1 | 387.1 | 366.3 | 97.2 | 90.6 | 20.8 | 0.10 | 63 | 100 | 32 |
| | 345 | 416.8 | 412.7 | 398.0 | 377.6 | 98.5 | 90.7 | 20.4 | −0.17 | 69 | 100 | 50 |
| Example 6 | 327 | 392.6 | 386.1 | — | 367.8 | 98.2 | 90.3 | 18.3 | — | 84 | 36 | — |
| | 324 | 387.4 | 381.5 | — | 363.9 | 97.8 | 90.2 | 17.6 | −0.23 | 84 | 36 | — |
| | 332 | 402.4 | 392.2 | — | 373.2 | 98.6 | 90.1 | 19.0 | −0.14 | 84 | 38 | — |
| Example 7 | 329 | 420.3 | 367.8 | — | 357.1 | 97.8 | 90.5 | 10.7 | — | 88 | 21 | — |
| | 326 | 414.2 | 365.2 | — | 354.4 | 97.5 | 90.4 | 10.8 | 0.03 | 75 | 18 | — |
| | 332 | 426.6 | 370.5 | — | 360.1 | 98.2 | 90.4 | 10.4 | 0.10 | 92 | 24 | — |
| Comparative Example 3 | 321 | 396.5 | 375.5 | — | 350.8 | 97.4 | 90.1 | 24.7 | — | 88 | 24 | — |
| | 316 | 387.3 | 369.0 | — | 346.1 | 96.4 | 89.6 | 22.9 | −0.36 | 71 | 18 | — |
| | 326 | 405.9 | 379.5 | — | 356.1 | 98.0 | 90.0 | 23.4 | 0.26 | 92 | 32 | — |
| Example 8 | 320 | 408.0 | 363.8 | — | 346.4 | 98.3 | 91.2 | 17.4 | — | 75 | 12 | — |
| | 316 | 403.1 | 358.3 | — | 343.2 | 97.8 | 91.0 | 15.1 | −0.58 | 71 | 0 | — |
| | 324 | 417.2 | 367.8 | — | 350.3 | 98.8 | 91.1 | 17.5 | −0.02 | 92 | 18 | — |
| Comparative Example 4 | 320 | 427.0 | 366.0 | — | 339.3 | 98.0 | 90.8 | 26.7 | — | 54 | 12 | — |
| | 316 | 413.0 | 351.0 | — | 334.6 | 96.8 | 90.4 | 16.4 | −2.58 | 50 | 0 | — |
| | 325 | 436.0 | 369.0 | — | 344.4 | 98.7 | 90.5 | 24.6 | 0.42 | 63 | 15 | — |
| Example 9 | 320 | 405.0 | 365.0 | — | 352.1 | 98.3 | 90.5 | 12.9 | — | 65 | 7 | — |
| | 325 | 390.0 | 362.0 | — | 346.9 | 97.5 | 90.1 | 15.1 | 0.44 | 50 | 2 | — |
| | 335 | 417.0 | 368.9 | — | 356.2 | 98.9 | 90.4 | 12.7 | 0.04 | 77 | 13 | — |
| Example 10 | 338 | 403.9 | 377.4 | — | 361.2 | 98.9 | 90.0 | 16.2 | — | 85 | 18 | — |
| | 335 | 395.1 | 377.8 | — | 359.4 | 98.6 | 90.0 | 18.4 | 0.73 | 85 | 17 | — |
| | 341 | 415.3 | 379.4 | — | 364.4 | 99.2 | 89.7 | 15.0 | 0.40 | 88 | 20 | — |
| Example 11 | 335 | 401.4 | 359.7 | — | 352.5 | 98.4 | 90.7 | 7.2 | — | 88 | 3 | — |
| | 330 | 390.2 | 356.6 | — | 356.2 | 97.5 | 90.2 | 0.4 | −1.36 | 88 | 0 | — |
| | 340 | 412.6 | 364.8 | — | 360.9 | 98.8 | 90.7 | 3.9 | 0.66 | 92 | 17 | — |

Although the present invention has been described in detail and by reference to specific embodiments, it is apparent to those skilled in the art that it is possible to add various alterations and modifications without departing from the spirit and the scope of the present invention.

The present application is based on Japanese Patent Application (No. 2018-75112) filed on Apr. 10, 2018, the entire contents of which are incorporated herein by reference. In addition, all references cited here are entirely incorporated.

The invention claimed is:

1. A method for producing at least one of an unsaturated aldehyde and an unsaturated carboxylic acid from an alkene by an oxidation reaction,
   wherein a n-layered catalyst layer (n≥2) is provided in a gas flow direction in a reaction tube,
   two or more kinds of catalysts having different activities are used; and
   the catalysts are packed in such a manner that dT≤20° C. is satisfied, when a difference between a temperature $PT_n$ of an exothermic peak in a n-th layer as counted from a gas inlet and a minimum value $mT_{n-1}$ of a temperature of a catalyst layer which appears between an exothermic peak in a (n−1)th layer and an exothermic peak in a n-th layer from the gas inlet is represented as dT $(=PT_n-mT_{n-1})$, and the change rate of dT is 2.5 or less at a reaction bath temperature within a range of ±6° C. of a reaction bath temperature at which the highest yield is obtained.

2. The method for producing at least one of an unsaturated aldehyde and an unsaturated carboxylic acid according to claim 1, wherein at the reaction bath temperature within a range of ±6° C. of the reaction bath temperature at which the highest yield is obtained, at least 10% of the catalysts in each catalyst layer is at a temperature equal to or higher than a temperature for switching of a rate-determining reaction in the oxidation reaction for producing at least one of the unsaturated aldehyde and the unsaturated carboxylic acid from the alkene.

3. The method for producing at least one of an unsaturated aldehyde and an unsaturated carboxylic acid according to claim 1, wherein at the reaction bath temperature within a range of ±6° C. of the reaction bath temperature at which the highest yield is obtained, at least 30% of the catalysts in each catalyst layer is at a temperature equal to or higher than the temperature for switching of the rate-determining reaction in the oxidation reaction.

4. The method for producing at least one of an unsaturated aldehyde and an unsaturated carboxylic acid according to claim 2, wherein a catalyst having a temperature for switching of the rate-determining reaction of 360° C. or lower in the oxidation reaction is used for the n-th catalyst layer.

5. The method for producing at least one of an unsaturated aldehyde and an unsaturated carboxylic acid according to claim 2, wherein at the reaction bath temperature within a range of ±6° C. of the reaction bath temperature at which the highest yield is obtained, at least 30% of the catalysts in each catalyst layer is at a temperature equal to or higher than the temperature for switching of the rate-determining reaction in the oxidation reaction.

6. The method for producing at least one of an unsaturated aldehyde and an unsaturated carboxylic acid according to claim 3, wherein a catalyst having a temperature for switching of the rate-determining reaction of 360° C. or lower in the oxidation reaction is used for the n-th catalyst layer.

\* \* \* \* \*